United States Patent [19]

Meyers

[11] 4,327,070
[45] Apr. 27, 1982

[54] PRODUCTION OF POTASSIUM FORMATE FROM POTASSIUM SULFATE

[75] Inventor: Robert A. Meyers, Tarzana, Calif.

[73] Assignee: TRW Inc., Redondo Beach, Calif.

[21] Appl. No.: 176,601

[22] Filed: Aug. 8, 1980

[51] Int. Cl.$^3$ .................. H02K 44/00; C07C 53/06
[52] U.S. Cl. ........................... 423/555; 310/11; 562/609
[58] Field of Search ............... 423/343, 555; 562/609; 310/11

[56] References Cited

U.S. PATENT DOCUMENTS

| 3,303,364 | 2/1967 | Hals ........................................ 310/11 |
| 3,928,537 | 12/1975 | Saitoh et al. ......................... 423/243 |
| 4,239,996 | 12/1980 | Bhada et al. ..................... 423/244 A X |

FOREIGN PATENT DOCUMENTS 381957 9/1923 Fed. Rep. of Germany ...... 562/609
50-83313 7/1975 Japan ................................. 562/609

*Primary Examiner*—G. O. Peters
*Attorney, Agent, or Firm*—Robert W. Keller; Patrick F. Bright

[57] ABSTRACT

A method for making water-soluble potassium formate substantially free of water-insoluble salts selectively and in high yield at temperatures at or below about 100° C., includes contacting potassium sulfate, potassium carbonate or a mixture of potassium and sodium carbonate and potassium and sodium sulfate with calcium formate, forming water-soluble potassium formate and water-insoluble calcium sulfate, calcium carbonate, or mixtures thereof, thus permitting recovery of substantially potassium-free calcium sulfate, calcium carbonate or both, and substantially calcium sulfate-free calcium carbonate-free potassium formate from the aqueous media.

4 Claims, 1 Drawing Figure

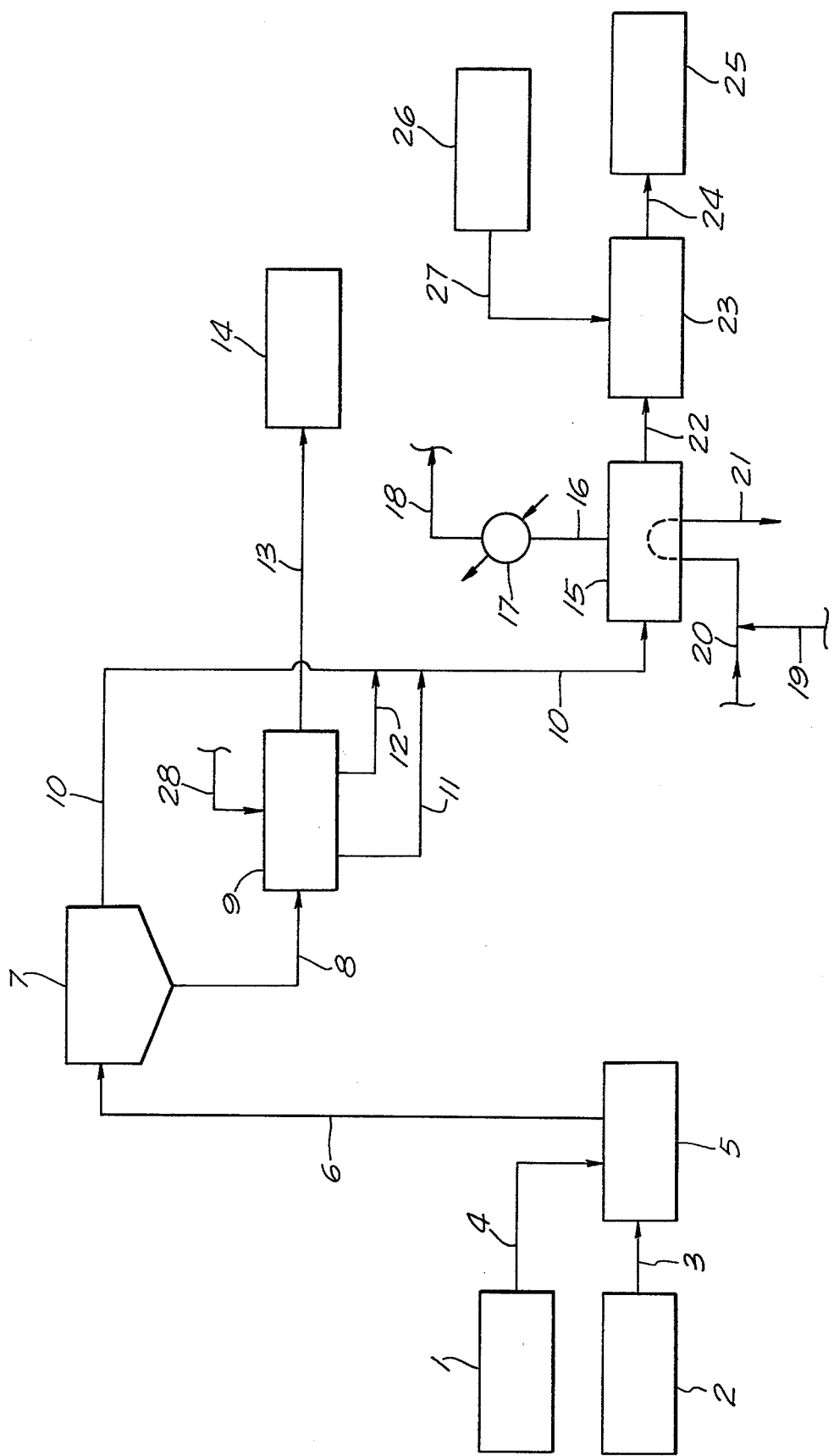

PRODUCTION OF POTASSIUM FORMATE FROM POTASSIUM SULFATE

This invention relates to a method for making potassium formate from potassium carbonate, potassium sulfate or both with substantially complete conversion of the potassium reactants to potassium formate. The method comprises reacting potassium sulfate, potassium carbonate or both with calcium formate in aqueous media at a temperature below about 100° C. The reaction proceeds rapidly, selectively and quantitatively, even at ambient pressures to form water-soluble potassium formate and water-insoluble calcium sulfate.

The potassium formate in solution is substantially free of sulfates and calcium; the water-insoluble calcium sulfate formed is substantially free of potassium, and precipitates rapidly. Minimal potassium loss to the precipitate is a great advantage of this process, for potassium is costly. After separation of the aqueous filtrate containing the water-soluble potassium formate from the water-insoluble calcium sulfate, potassium formate can be recovered by crystallization or other known techniques. Alternatively, the aqueous filtrate can be fed directly to an MHD reactor as a source of potassium for the charged potassium ion flux needed in such reactors.

Our new method also works well where sodium sulfate, sodium carbonate, or both, are present in the aqueous media. Spent MHD seed includes both of these species. In our process, the sodium salts convert to sodium formate, which are carried with, but do not interfere with, say, the potassium formate.

The method of this invention works well for reactions of potassium alone or potassium and sodium carbonate with calcium formate in aqueous media at temperatures below about 100° C. As with potassium or potassium and sodium sulfate, the reaction produces water-soluble potassium formate or potassium and sodium formate, but instead of calcium sulfate, forms water-insoluble calcium carbonate. As with the calcium sulfate, the calcium carbonate produced by our process is substantially free of potassium and sodium. The potassium formate or potassium formate/sodium formate produced is substantially free of calcium and calcium carbonate. As with the sulfates, the calcium carbonate precipitates rapidly, and the aqueous media containing the water-soluble potassium or potassium and sodium formate can be separated therefrom and treated for recovery of the formate salts. Alternatively, the aqueous formate or potassium and sodium formates can be fed directly to an MHD reactor as a source of the potassium reactant needed there.

Our new process works well with potassium and sodium sulfate and potassium and sodium carbonate obtained as spent seed from MHD reactors. Our process works well with potassium and sodium carbonates and sulfates from other sources, too. Spent seed from an MHD reactor commonly contains both potassium sulfate and potassium carbonate and much smaller amounts of sodium sulfate and potassium sulfate, and our process is particularly effective with this mixture of salts.

Generally, our new process works at temperatures below about 100° C., and will produce a 90% or higher recovery of the potassium or potassium/sodium reactants. However, our preferred temperature range is about 20° C., to about 80° C. Although there is no need to impose any pressure above atmospheric on the reactants, the reaction proceeds well at pressures in the range of about 1 to about 3 atmospheres. Increasing the temperature of the reaction accelerates the reaction. Increasing the pressure has a similar though less pronounced effect.

Our process can better be understood by reference to the drawing. In the drawing, spent seed recovered from an MHD combustor as a solid is fed from storage zone 1 via line 4 to reactor 5. There, the potassium (with minor amounts of sodium) sulfate/potassium carbonate spent seed is mixed with aqueous calcium formate fed to reactor 5 from storage zone 2 via line 3. In reactor 5, potassium sulfate and potassium carbonate react with calcium formate to form potassium formate. (Minor amounts of sodium sulfate and carbonate are present throughout this process. Accordingly, the product formate includes minor amounts of sodium formate.) Substantially no separation of insoluble calcium sulfate or calcium carbonate from the aqueous media takes place in reactor 5. Instead, the aqueous media containing the reaction products is fed via line 6 to clarifier 7. From there, water-insoluble calcium carbonate and sulfate are recovered via line 8, with the water-soluble potassium formate passing in aqueous media via line 10 to triple-effect evaporator 15.

The solids and seed solution taken from clarifier 7 via line 8 pass to filtration and washing zone 9, to which wash water is added via line 28. Solids are taken from filtration/washing zone 9 via line 13 to solids disposal zone 14. The filtrates and wash filtrates taken from filtration/washing zone 9 via lines 11 and 12, respectively, are combined with the overflow from clarifier 7 passing via line 10 to triple-effect evaporator 15.

In triple-effect evaporator 15, potassium formate salts are concentrated using steam that is fed to evaporator 15 via lines 19 and 20. Water condensate is recovered from evaporator 15 via line 21. Condensate is also recovered from evaporator 15 overhead via line 16, passes through cooler 17, and is taken to recovery via line 18.

The concentrated potassium formate-containing aqueous media passes from evaporator 15 via line 22 to mixing tank 23, to which makeup potassium carbonate from storage zone 26 is added via line 27. Resulting MHD seed containing potassium formate and potassium carbonate passes to MHD reactor 25 via path 24.

EXAMPLES

We formulated 100 ml of a synthetic spent MHD seed solution to contain 0.55 mole potassium sulfate and 0.21 mole sodium sulfate. The relative amounts of sodium and potassium sulfate in this synthetic MHD seed solution are much the same as in actual spent MHD seed. We added no carbonates to this synthetic seed, however, because carbonates complicate analysis of the calcium sulfate precipitate formed. We then mixed this synthetic spent MHD seed solution with a stoichiometric amount of calcium formate in water, and allowed the resulting reaction to proceed for 30 minutes at 60° C. Immediately upon mixing the reactants, solid gypsum (calcium sulfate dihydrate) began precipitating from the aqueous media. After 30 minutes, calcium sulfate precipitation appeared complete.

We analyzed the precipitate to identify its nature and measure any potassium losses. Our analysis showed that the precipitate, after washing on a filter, consisted of 99% pure gypsum by weight, only 0.2% potassium by weight and 0.2% sodium by weight. If we omitted washing the precipitate on a filter, the precipitate contained 0.4 to 0.6% potassium by weight.

To determine whether or not any potassium/calcium double salts such as syngenite had formed, we subjected the precipitate to x-ray diffraction analysis. That analysis, set forth in Table I below, shows that the precipitate contained substantially no syngenite.

We then analyzed the filtrate obtained from the reaction, and found that the concentration of calcium sulfate there closely approximated its solubility in water. We calculated that our process removes 94.5% of the sulfate in the form of precipitated gypsum. See Table II below.

In a second run performed on the same synthetic spent seed solution, we utilized a less than stoichiometric amount of calcium formate to assure leaving some sulfate in solution. In particular, we reacted a 15% molar excess of synthetic spent seed with calcium formate for 30 minutes at 60° C. As before, the solid precipitate obtained was washed with water on a filter and analyzed. Again, the yield of gypsum was approximately 92%; this gypsum had a purity exceeding 99%. The potassium losses were less than 0.2% by weight. Table III below summarizes these two examples, and shows that our process proceeds rapidly, selectively and quantitatively to produce substantially potassium-free calcium sulfate.

TABLE I

X-RAY DIFFRACTION ANALYSIS OF CALCIUM SULFATE PRECIPITATE FROM RUN 1

| $2\theta$ | $d\text{Å}$ | Experimental | Calcium Sulfate* Dihydrate (Gypsum) Literature, I |
|---|---|---|---|
| 11.6 | 7.62 | 100 | $7.56_{100}$ |
| 20.7 | 4.29 | 70 | $4.27_{50}$ |
| 23.1 | 3.85 | 18 | — |
| 23.3 | 3.81 | 30 | $3.79_{20}$ |
| 29.0 | 3.08 | 60 | $3.06_{55}$ |
| 31.0 | 2.88 | 24 | $2.87_{25}$ |
| 32.0 | 2.79 | 8 | $2.78_6$ |
| 33.0 | 2.71 | 20 | $2.68_{28}$ |
| 34.4 | 2.60 | 4 | $2.59_4$ |
| 35.9 | 2.50 | 8 | $2.50_6$ |
| 36.6 | 2.45 | 4 | $2.45_4$ |
| 37.3 | 2.41 | 2 | $2.40_4$ |
| 40.6 | 2.22 | 10 | $2.22_6$ |
| 43.4 | 2.08 | 12 | $2.08_{10}$ |
| 47.8 | 1.90 | 10 | $1.90_{16}$ |
| 48.4 | 1.88 | 6 | $1.88_{10}$ |
| 50.3 | 1.81 | 10 | $1.81_{10}$ |

*Presence of potassium calcium sulfate (syngenite) requires a line at d-value of 3.16.

TABLE II

ANALYSIS OF SYNTHETIC MHD SEED SOLUTION FROM RUN 1 BEFORE AND AFTER REGENERATION

| | Moles | | | |
|---|---|---|---|---|
| | K | Na | $SO_4$ | Ca |
| Analyzed spent seed solution | 0.110 | 0.042 | 0.076 | 0.076 |
| Analyzed regenerated seed solution | 0.120 | 0.046 | $0.007^c$ | 0.004 |
| Calculated, regenerated seed solution based on solid gypsum yield | 0.110 | 0.042 | $0.009^a$ | $0.009^a$ |
| Calculated, based on gypsum solubility$^b$ | — | — | 0.003 | 0.003 |

$^a$Based on 11.6g yield (0.076 moles) of precipitated gypsum.
$^b$0.241g/100cc in cold $H_2O$.
$^c$94.5% of theoretical removal: $\frac{0.076 - 0.007}{0.076 - 0.003} \times 100$

TABLE III

POTASSIUM RECOVERY AND SULFATE REMOVAL FROM SYNTHETIC MHD SEED BY OUR PROCESS

| Run | Precipitate Weight, g | Precipitate Analysis, % W/W | | | | Potassium Recovery in Solution (based on loss to precipitate) |
|---|---|---|---|---|---|---|
| | | Ca | $SO_4$ | Na | $K^d$ | |
| $1^b$ | $11.6^a$ | 23 | 55 | 0.19 | 0.21 | 99.5% |
| $2^c$ | $18.6^a$ | 23 | 53 | 0.21 | 0.22 | 99.5% |
| Theoretical, if pure gypsum | | 23 | 56 | 0 | 0 | — |

$^a$Reaction time of 60° C., for 30 minutes, cool, then filter and wash twice on filter with two 50 ml portions of $H_2O$.
$^b$100 ml solution 0.55 M in $K_2SO_4$ and 0.21 M in $Na_2SO_4$ mixed with 100 ml of 0.76 M Ca $(HCO_3)_2$ solution.
$^c$100 ml solution 0.99 M in $K_2SO_4$ and 0.39 M in $Na_2SO_4$ mixed with 100 ml of 1.2 M Ca $(HCO_3)_2$; a 15% molar excess of sulfate.
$^d$If no washing on filter, residual K is 0.4 to 0.6% W/W.
A 92% yield of gypsum:
Run 1 $\frac{0.067 \text{ moles ppt}}{0.076 - 0.003 \text{ theor}} \times 100$;
Run 2 $\frac{0.108 \text{ moles ppt}}{0.120 - 0.003 \text{ theor}} \times 100$.

What is claimed is:

1. A method comprising contacting, in aqueous media at a pressure in the range of about 1.0 to about 3 atmospheres and at a temperature of not more than about 100° C., spent seed from an MHD reactor including potassium sulfate with calcium formate to form water-soluble potassium formate and water-insoluble calcium sulfate, separating said calcium sulfate, substantially free of potassium, from said aqueous media; and feeding the aqueous, water-soluble potassium formate to an MHD reactor as a potassium source.

2. The method of claim 1 wherein the reaction temperature is in the range of about 20° C., to about 80° C.

3. The method of claim 1 wherein the aqueous media also includes sodium sulfate and potassium and sodium carbonates, said contacting produces water-insoluble calcium carbonate and calcium sulfate, and said separating step also removes calcium carbonate and calcium sulfate, substantially free of potassium, from said aqueous media.

4. A method comprising contacting, in aqueous media at a temperature of not more than about 100° C., spent seed from an MHD reactor including a compound selected from the group consisting of potassium sulfate, sodium sulfate, potassium carbonate, sodium carbonate and mixtures thereof with calcium formate to form water-soluble potassium formate and sodium formate and water-insoluble calcium salts, recovering said water-soluble potassium and sodium formates substantially free of calcium salts, recovering calcium salts substantially free of potassium from said aqueous media, and feeding said potassium and sodium formates to an MHD reactor as a potassium source.

* * * * *